United States Patent [19]
Andrews et al.

[11] Patent Number: 5,616,777
[45] Date of Patent: Apr. 1, 1997

[54] CHIRAL HYDRAZINE DERIVATIVES

[75] Inventors: David R. Andrews, Maplewood; Anantha Sudhakar, East Brunswick, both of N.J.

[73] Assignee: Schering Corporation, Kenilworth, N.J.

[21] Appl. No.: 425,129

[22] Filed: Apr. 19, 1995

[51] Int. Cl.$^6$ .................. C07C 269/04; C07C 243/12
[52] U.S. Cl. ............................. 560/29; 564/464
[58] Field of Search ................. 560/29; 564/464

[56] References Cited

U.S. PATENT DOCUMENTS 5,039,676  8/1991  Saksena et al. .................. 514/254
5,403,937  4/1995  Saksena et al. .................. 548/268.8

FOREIGN PATENT DOCUMENTS

WO89/04829  6/1989  WIPO.
WO93/09114  5/1993  WIPO.
WO94/25452  11/1994  WIPO.

OTHER PUBLICATIONS

Greene, et al., "Protective Groups in Organic Synthesis", 2 ed., pp. 10–142, John Wiley & Sons (New York, 1991).
"Optical Resolution Procedures for Chemical Compounds, vol. 1, Amines and Related Compounds", pp. 7–24, Optical Resolution Information Center, Riverdale, New York.
Kobayaski, et al., *Bull. Chem. Soc. Jpn.*, 62, 3038–3040 (1989).

*Primary Examiner*—Joseph Conrad
*Attorney, Agent, or Firm*—John H. C. Blasdale; Norman C. Dulak; Anita W. Magatti

[57] ABSTRACT

Disclosed are chiral hydrazine derivatives of the formula (Ia), (Ib), (Ic) and (Id)

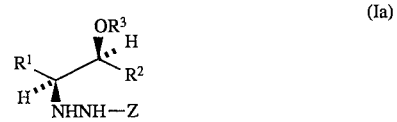

(Ia)

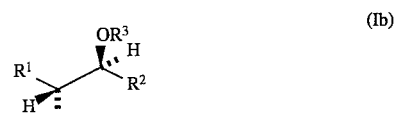

(Ib)

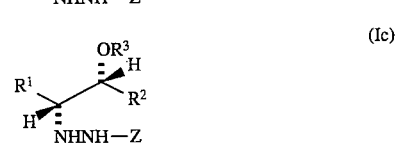

(Ic)

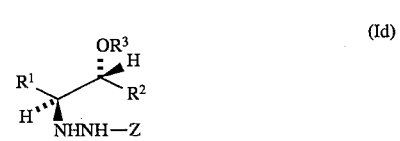

(Id)

wherein:

$R^1$ and $R^2$ are independently $C_1$–$C_{10}$ alkyl;

$R^3$ is H or $R^4$ wherein $R^4$ is a hydroxy protecting group; and

Z is H, —CHO, —C(O)OC(CH$_3$)$_3$ or —C(O)OCH$_2$C$_6$H$_5$.

Also described is a process for preparing chiral hydrazines of the formula (Ia), (Ib), (Ic) and (Id).

8 Claims, No Drawings

CHIRAL HYDRAZINE DERIVATIVES

The present invention comprises a process for preparing chiral hydrazine derivatives useful as intermediates for the synthesis of tri-substituted tetrahydrofuran triazole antifungal agents.

BACKGROUND OF THE INVENTION

PCT International Publication No. WO 89/04829, U.S. Pat. No. 5,039,676, and PCT International Publication No. WO 93/09114 disclose triazolone containing substituted tetrahydrofuran azole and imidazole compounds having utility as antifungal agents. A number of processes for the synthesis of these compounds are known.

PCT International Application No. PCT/US92/08981 discloses a process for the synthesis of tri-substituted tetrahydrofuran azole antifungals comprising converting a compound of the formula

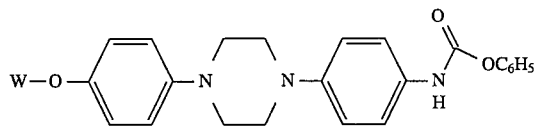

wherein W represents

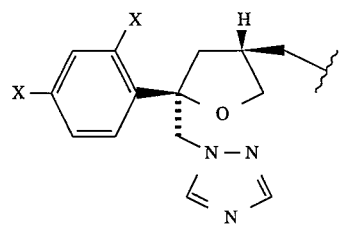

to a compound of the formula

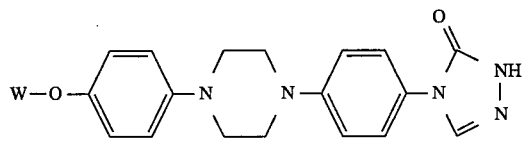

which is subsequently N-alkylated to give a compound of the formula

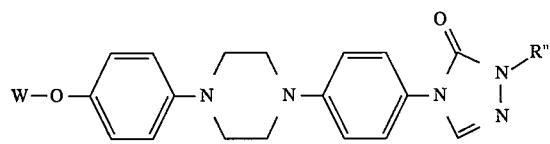

wherein R" is as defined therein.

N-alkylation of the triazolone group as described in the prior art is inefficient, requiring a large excess of an expensive alkylating agent, typically an alkyl bromide, and results in a mixture of N-alkylated and O-alkylated products, necessitating laborious purification methods and giving low yields of the N-alkylated triazolone. These problems can be avoided by constructing the triazolone system with the N-alkyl group already in place.

Co-owned co-pending U.S. Ser. No. 08/458,550 discloses a process for preparing N-alkyl triazolones comprising reacting a carbamate of the formula

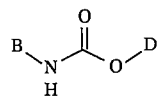

wherein:
B is aryl, substituted aryl or a group of the formula

wherein R is $CH_3$, H or a group of the formula

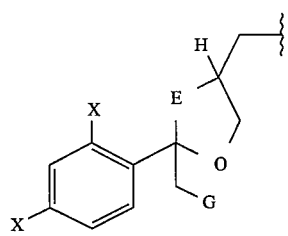

wherein G is imidazolyl or triazolyl, E is $CH_2$ or O, and each X is independently F or Cl; and D is $C_1$–$C_6$ alkyl, aryl, substituted aryl or aryl($C_1$–$C_6$ alkyl); with a hydrazine derivative of the formula Z—NH—NH—$R^5$, wherein $R^5$ is $C_1$–$C_{20}$ alkyl or substituted $C_1$–$C_{20}$ alkyl, and Z is —CHO, —C(O)OC(CH$_3$)$_3$ or —C(O)OCH$_2$C$_6$H$_5$, to form a triazolone of the formula

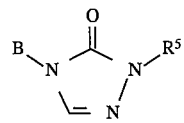

wherein B and $R^5$ are as defined above.

However, for preparing compounds wherein the N-alkyl substituent $R^5$ comprises one or more chiral centers a source of an appropriate chiral hydrazine derivative is needed.

SUMMARY OF THE INVENTION

The present invention solves the aforementioned problems by providing chiral hydrazine derivatives for use in preparing chiral N-alkyl triazolones. Also provided is a stereoselective and chemically efficient process for preparing said chiral hydrazine derivatives.

The chiral hydrazine derivatives of the present invention are compounds of the formula (Ia), (Ib), (Ic) and (Id)

(Ia)

(Ib)

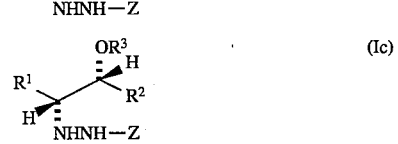

(Ic)

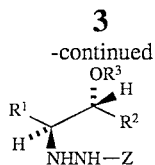

(Id)

wherein:

R¹ and R² are independently $C_1$–$C_{10}$ alkyl;

R³ is H or R⁴ wherein R⁴ is a hydroxy protecting group; and

Z is H, —CHO, —C(O)OC(CH₃)₃ or —C(O)OCH₂C₆H₅.

Preferred are compounds of the formula (Ia), (Ib), (Ic) and (Id) wherein R¹ is $C_1$–$C_4$ alkyl, R² is $C_1$–$C_4$ alkyl. Also preferred are compounds of the formula (Ia), (Ib), (Ic) or (Id) wherein R³ is H or R⁴ wherein R⁴ is benzyl.

Particularly preferred are compounds of the formula (Ia), (Ib), (Ic) and (Id), wherein Z is —CHO or —C(O)OC(CH₃)₃, and R³ is H or benzyl. Also particularly preferred are compounds of the formula (Ia), (Ib), (Ic) and (Id) wherein Z is H and R³ is H or benzyl.

Most preferred are compounds of the formula (Ia).

The present invention also provides a process for preparing a chiral hydrazine derivative of the formula (Ia) or (Ib)

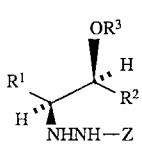

(Ia)

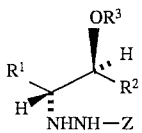

(Ib)

wherein R¹, R², R³ and Z are as defined, above comprising the steps:

(a) reacting a chiral compound of the formula (II)

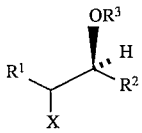

(II)

wherein X is a leaving group and R¹, R² and R³ are as defined above, with hydrazine, to form a mixture of diastereomeric hydrazines of the formulae

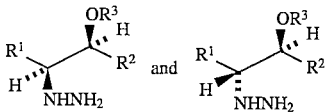

and treating the mixture with a chiral acid to isolate the desired diastereomer as its chiral acid salt; and (b) treating the chiral acid salt of step (a) with a compound of the formula Y—Z, wherein Z is —CHO, —C(O)OC(CH₃)₃ or —C(O)OCH₂C₆H₅, and Y is a leaving group, to form the chiral hydrazine derivative.

In an alternative embodiment, chiral hydrazine derivatives of the formula (Ic) or (Id)

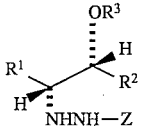

(Ic)

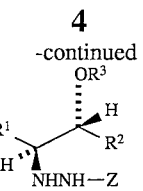

(Id)

wherein R¹, R², R³ and Z are as defined above, are prepared via the same process by substituting a chiral compound of the formula (III)

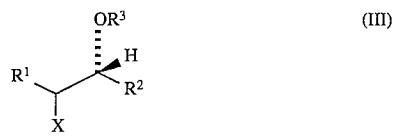

(III)

for compound (II) in step (a).

DETAILED DESCRIPTION

All of the publications cited herein are hereby incorporated in their entirety by reference.

As used herein, the term:

"alkyl" means a straight or branched alkyl chains having the indicated number of carbon atoms; and "substituted alkyl" means an alkyl group bearing one to three substituents selected from halo, $C_1$–$C_6$ alkoxy and aryloxy;

"aryl" means a carbocyclic aromatic group, such as phenyl or naphthyl; and "substituted aryl" means an aryl group bearing one to three substituents selected from halo, nitro, $C_1$–$C_6$ alkyl and $C_1$–$C_6$ alkoxy;

"halo" means a chloro, bromo or iodo group;

"aryl(alkyl)" means an alkyl group substituted by an aryl group, benzyl for example;

"hydride reducing agent" means a metal hydride reagent, such as NaBH₄, Red—Al, DIBAL—H, LiBH₄, NaBH₃CN, zinc borohydride, calcium borohydride, a combination of LiBH₄ and ZnBr₂, or a combination of NaBH₄ and LiCl; and "tertiary amine base" means bases such as pyridine, Et₃N, DMAP or Hünigs base, as well as analogous polymer supported bases comprising one or more tertiary amino groups.

As used herein the following reagents and solvents are identified by the abbreviations indicated: methanol (MeOH); t-butyl methyl ether (TBME); triethylamine (Et₃N); sodium bis(2-methoxyethoxy)aluminum hydride (Red—Al); di-isobutylaluminum hydride (DIBAL—H); di-isopropylethylamine (Hünigs base); 1,2-dimethoxyethane (DME); 1,8-diazabicyclo[5.4.0]undec-7-ene (DBU); ethanol (EtOH); 1,4-diazabicyclo[2.2.2]octane (Dabco); tetrabutylammonium hydroxide (Bu₄NOH); dibenzoyl-L-tartaric acid (L—DBTA); dibenzoyl-D-tartaric acid (D—DBTA); 1,5-diazabicyclo[4.3.0]non-5-ene (DBN); pyridinium p-toluenesulfonate (PPTS); N-t-butoxycarbonylhydrazine (BOC—hydrazine); di-p-toluoyl-D-tartaric acid (D—DTTA); di-p-toluoyl-L-tartaric acid (L—DTTA).

The "hydroxyl protecting group", R⁴, is a protecting group which blocks an —OH group thereby preventing reactions involving the —OH group from occurring during the process of the present invention. Hydroxyl protecting groups are well known in the art and methods for the formation and removal of hydroxyl protecting groups are also well known, such as those described in Greene, et al., "Protective Groups in Organic Synthesis", 2nd ed., John Wiley & Sons, 10–142 (New York 1991). Preferred hydroxyl protecting groups for use in the present invention are ethers, such as benzyl ether.

The term "leaving group" means a substituent which is susceptible to displacement by a suitable nucleophile, and includes groups such as halo; $C_1-C_6$ alkoxy; $-OS(O)_2R^5$ wherein $R^5$ is $C_1-C_4$ alkyl, $CF_3$, aryl, substituted aryl or aryl($C_1-C_4$ alkyl); or $-OC(O)R^6$ wherein $R^6$ is $C_1-C_6$ alkyl, $C_1-C_6$ alkoxy, aryl or substituted aryl. The particular leaving group to be used is in part dependent upon the strength of the nucleophile, with more labile groups, such as halo and in particular $-OS(O)_2R^5$, being used in conjunction with weaker nucleophiles. The leaving group X is preferably a group of the formula $-OS(O)_2R^5$, wherein $R^5$ is as defined above, and is more preferably such a group wherein $R^5$ is selected from $-CH_3$, $-CF_3$, $-C_6H_5$, $-C_6H_4CH_3$, $-C_6H_4Br$ and $-C_6H_4Cl$. The leaving group Y is preferably: $C_1-C_6$ alkoxy when Z is $-CHO$; halo when Z is $-C(O)OCH_2C_6H_5$; and $-OC(O)R_6$, wherein $R^6$ is $-OC(CH_3)_3$, when Z is $-C(O)OC(CH_3)_3$.

The "chiral acid" used in the present invention is a single stereoisomer of a chiral acid which can be used to resolve a mixture of diastereomeric substituted hydrazines, such as those listed in Newman, "Optical Resolution Procedures for Chemical Compounds, Vol. 1., Amines and Related Compounds", pp. 7–24, Optical Resolution Information Center, Riverdale, N.Y. Preferred chiral acids include L—DBTA, D—DBTA, L—DTTA and D—DTTA.

The "organometallic alkylating agent" of formula $R^1$-M is an alkyl metal compound comprising an alkyl group $R^1$, as defined above, a carbon atom of which is directly bonded to a metallic element such as Li, Na, K, Cs, Mg or Zn, and which is capable of reacting with the carbonyl carbon of an amide to introduce an alkyl radical thereby forming a ketone. Preferred organometallic alkylating agents include Grignard reagents, e.g. where M is MgBr, MgCl or MgI, and organolithium reagents, e.g. where M is Li.

A "halogenating agent" is a compound capable of converting a hydroxy group to a halo group. Preferred halogenating agents include $PCl_5$, $PCl_3$, $SOCl_2$, $PBr_3$.

A "sulfonyl halide" is a compound of the formula $R^5S(O)_2$-L, wherein $R^5$ is as defined above and L is halo.

The present invention provides a process for preparing compounds of the formula (Ia) or (Ib) as shown in Reaction Scheme 1. The present invention also provides a process for preparing compounds of the formula (Ic) or (Id) via essentially the same process as shown in Reaction Scheme 1.

Reaction Scheme 1

Step A:

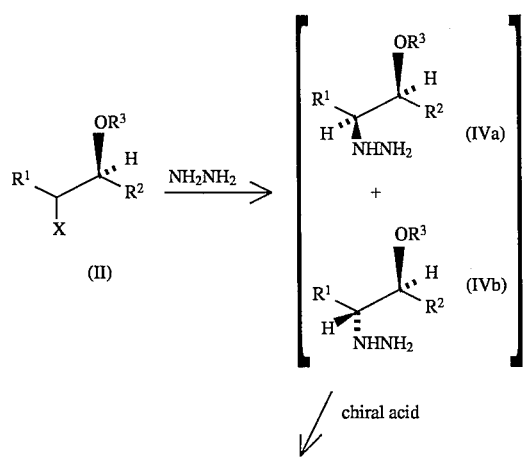

-continued
Reaction Scheme 1

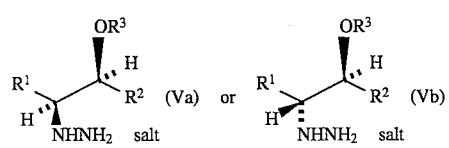

Step B:

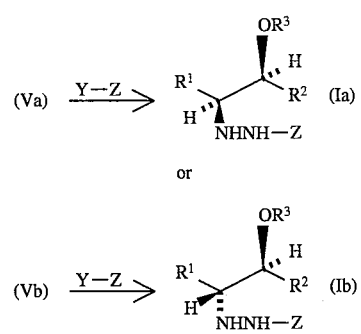

In Step A of Reaction Scheme 1, a chiral compound of the formula (II), wherein $R^3$ is $R^4$, and $R^1$, $R^2$, $R^4$ and X are as defined above, is treated with hydrazine, preferably as the monohydrate, in a $C_1-C_6$ alcohol solvent, preferably EtOH, MeOH or iPrOH, at a temperature of 25° to 100° C., preferably at 40° to 80° C., and most preferably at 60° to 70° C., to form a diastereomeric mixture of hydrazines (IVa) and (IVb). The mixture of diastereomers is resolved by treating with a chiral acid to give the chiral acid salt of a single diastereomer (Va) or (Vb). The chiral acid treatment is carried out in a solvent suitable for selective crystallization of the chiral acid salt, such as water, a $C_1-C_6$ alcohol, acetone, TBME, DME, ether, EtOAc, or a combination of two such solvents, such that the salt of one diastereomer crystallizes from solution while the salt of the other diastereomer is left in solution. Preferably the chiral acid and solvent are selected such that the desired diastereomer (Va) or (Vb) selectively crystallizes leaving the unwanted diastereomer in solution. To the extent that the crystallization is only partially selective for the desired diastereomeric salt, the optical purity of salt can be increased by recrystallization of the salt (Va) or (Vb) from a suitable solvent.

In Step B, the appropriate chiral salt (Va) or (Vb) obtained from Step A is treated with a compound of the formula Y—Z, wherein Y and Z are as defined above, at a temperature of 20° to 120° C., preferably at 30° to 90° C., and most preferably at 40° to 70° C., to form a compound of the formula (Ia) or (Ib), respectively, wherein $R^3$ is $R^4$, which is optionally deprotected to form a compound of the formula (Ia) or (Ib) wherein $R^3$ is H. The reaction is regioselective, occurring selectively at the primary nitrogen atom of the hydrazine rather than the secondary nitrogen.

Alternatively, for preparing a compound of the formula (Ic) or (Id), a compound of the formula (III)

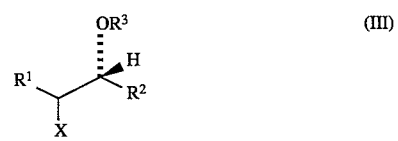

wherein $R^1$, $R^2$, $R^3$ and X are as defined above, is treated with hydrazine via essentially the same procedure as described for compound (II) in Step A of Reaction Scheme I to regioselectively form a mixture diastereomeric hydrazines of the formula (IVc) and (IVd)

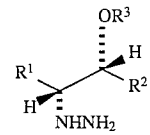

(IVc)

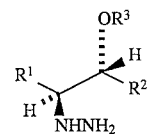

(IVd)

which are treated with a chiral acid via essentially the same conditions as described in Step A to give the chiral salt of a single diastereomer (Vc) or (Vd)

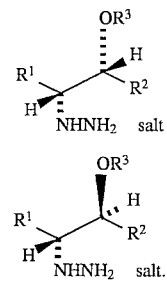

The appropriate chiral salt (Va) or (Vb) obtained from Step A is treated with a compound of the formula Y—Z via essentially the same process as described for Step B or Reaction Scheme 1 to form a compound of the formula (Ic) or (d), respectively.

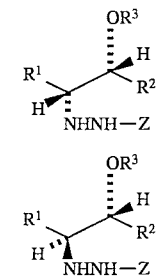

As an alternative, Step B of Reaction Scheme 1 can be carried out using the free hydrazine (IVa), (IVb), (IVc) or (IVd) in place of the salt. The free hydrazine can be obtained as a mixture of diastereomers by omitting the chiral acid treatment from Step A, or the salt of a single isomer (Va), (Vb), (Vc) or (Vd) can be treated with a suitable base using standard methods to regenerate the chiral hydrazine (IVa), (IVb), (IVc) or (IVd) as a single isomer.

Chiral starting compounds of the formula (II) and (III) are known or can be readily prepared from known compounds via established methods. For example, a compound of the formula (II) can be prepared from a compound of the formula (VI) via the procedure shown in Reaction Scheme 2.

Reaction Scheme 2

Step A:

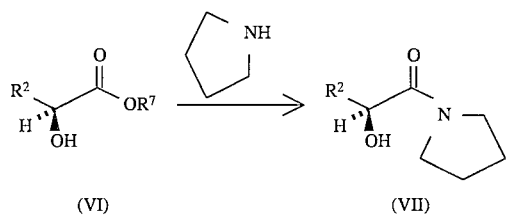

Step B:

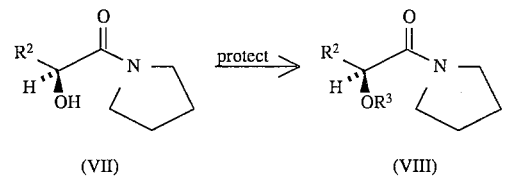

Step C:

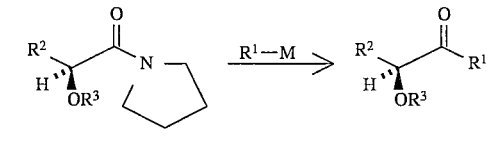

Step D:

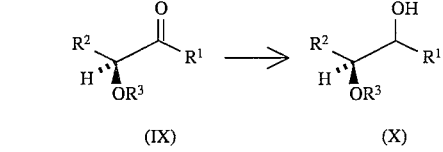

Step E:

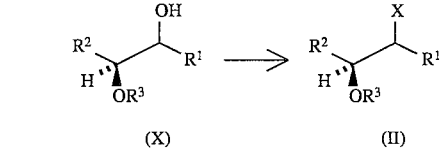

In Step A of Reaction Scheme 2, a compound of the formula (VI) wherein $R^2$ is as defined above and $R^7$ is $C_1$–$C_6$ alkyl, i.e., the (S)-isomer of a chiral hydroxy ester, is treated with pyrrolidine via substantially the same procedure described in Kobayashi, et al., *Bull Chem. Soc. Jpn.*, 62, 3038–3040 (1989), to form the (S)-hydroxyamide (VII).

In Step B, the hydroxyl group of the amide (VII) is protected with a suitable protecting group to form a compound of the chiral formula (VIII) wherein $R^3$ is $R^4$. Methods for the protection of hydroxyl groups are described in Greene, et al., supra.

In Step C, compound (VIII) is treated with an organometallic alkylating agent of the formula $R^1$-M, wherein $R^1$ is as defined above, and M represents Li, Na, K, Cs, MgBr, MgCl, MgI, in a suitable solvent, such as $Et_2O$, THF, toluene, DME or dioxane, at a temperature of –80° to 50° C., preferably at –40° to 20° C., and most preferably at –30° to 10° C., to give a chiral ketone of the formula (IX).

In Step D, the ketone (IX) is treated with a hydride reducing agent, in a suitable solvent, such as $Et_2O$, THF, DME, dioxane, or a $C_1$–$C_6$ alcohol, at a temperature of –80° to 100° C., preferably at −40° to 80° C., and most preferably at −20° to 70° C., to form the alcohol (X). The choice of solvent and temperature is dictated by the specific hydride reducing agent used.

In Step E, the alcohol (X) is converted to a compound of the formula (II) via procedures well known in the art. For example, a compound of the formula (II) wherein X is halo can be prepared by treating compound (X) with a halogenating agent, such as $PCl_5$ or $SOCl_2$. Compounds of the formula (II) wherein X is $-OS(O)_2R^5$, and $R^5$ is as defined above, can be prepared by treating compound (X) with a sulfonyl halide of the formula $R^5S(O)_2Cl$ or $R^5S(O)_2Br$, wherein $R^5$ is as defined above, in the presence of a tertiary amine base.

In an analogous manner, compounds of the formula (III) can be prepared by using the enantiomer of compound (VI) in the process of Reaction Scheme 2, i.e., by using a compound of the formula (XI)

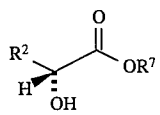
(XI)

wherein $R^2$ and $R^7$ are as defined above.

Chiral compounds of the formula (VI and XI) are known and can be prepared via methods well known in the art. Compounds of the formula $R^1$-M and Y—Z are known and are commercially available or can be prepared via established methods.

The following preparations and examples are illustrative of the process of the present invention.

EXAMPLE 1

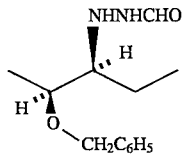

Step A:

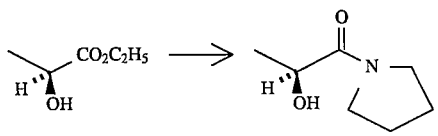

The chiral benzyloxyamide is prepared from ethyl (S)-lactate via substantially the same procedure as described in Kobayashi, et al., *Bull. Chem Soc. Jpn.*, 62, 3038–3040 (1989).

Step B:

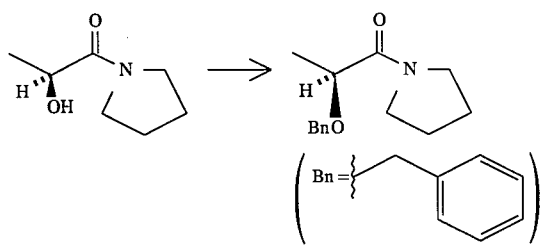

The product of Step A is converted to the corresponding benzyl ether via procedures such as the described in Kobayashi, et al., supra. Alternatively, benzylation can be carried out via other methods known in the art such as those described in Greene, et al., "Protective Groups in Organic Synthesis", 2nd edition, p. 47–49, John Wiley & Sons, New York, (1991).

Step C:

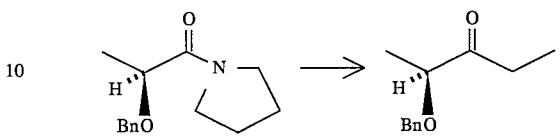

Combine 16 L of anhydrous THF and 12.5 kg of the 2-(S)-benzyloxyamide from Step B under nitrogen atmosphere and stir while cooling to −10° to −5° C. Slowly (over a period of 60 to 90 min.) add 58.4 kg of ethyl magnesium bromide as a 1 M solution in THF such that the temperature remains at −10° to −3° C. Stir the reaction mixture at −4° to −2° C. for 3 to 5 hours. Slowly add the reaction mixture to a stirred mixture of 125 L of MTBE and 7 L of acetic acid at −10° to −5° C. such that the temperature remains at 0° to 15° C. Stir the mixture for another 20 to 30 min., then add a combination of 12.5 L of MTBE, 1.25 L of HOAc and 50 mL of water. Agitate the mixture, then allow it to settle and separate the organic and aqueous layers. Wash the organic layer successively with 50 L of water, 50 L of 5% $NaHCO_3$ (aqueous), and 50 L of water. Concentrate the organic layer to a volume of 25 L via distillation at 55° to 60° C., add 25 L of MTBE and cool to <30° C. Concentrate again to a volume of 25 L then concentrate in vacuo (at a temperature of about 50° C.) to give the ketone product as a residue.

Dissolve the product in 15 L of DME to give a solution of the product for use in Step D.

Step D:

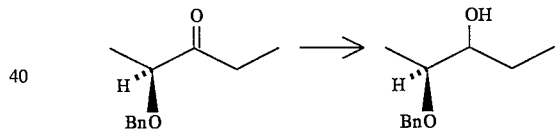

Combine 103 L of DME and 12 kg of $ZnBr_2$ and heat the mixture to 60° to 65° C. to dissolve the solids. Cool the mixture to 25° to 30° C. Slowly add this solution to a mixture of 1.24 kg of $LiBH_4$ and 21 L of DME at 0° to 10° C. such that the temperature remains at 0° to 15° C. Cool the resulting mixture to −5° to 5° C. and stir for 40 to 50 min. Slowly add the product solution from Step C such that the temperature remains at −5° to 5° C. Stir the mixture until the reaction is complete by HPLC. [HPLC analysis procedure: Dilute a 0.5 mL aliquot of the reaction mixture to a volume of 250 mL with the mobile phase MeOH/water/$H_3PO_4$ (50:50:0.1) and analyze 5 µL of that solution using a Zorbax® RX-ODS column and a U.V. detector.] Slowly add 15 L of acetone such that the temperature remains at 0° to 20° C. Slowly add the resulting mixture to a stirred mixture of 21 L of water and 21 kg of ice such that the temperature remains at 5° to 15° C. Slowly add a mixture of 10 L of conc. HCl, 83 L of water and 21 kg of ice, keeping the temperature at 5° to 15° C., then stir for 20 min. Add 103 L of MTBE and stir for 20 min. Allow the mixture to settle and separate the aqueous and organic layers. Extract the aqueous layer with 44 L of MTBE and combine the organic layers. Wash with water (4×41 L), then concentrate the organic solution via distillation at a temperature of <55° C. to a volume of 12.5

L. Add 21 L of MTBE and again concentrate to a volume of 12.5 L. Concentrate in vacuo at a temperature of <50° C. to give a mixture of the diastereomeric 2(S)-3(S)- and 2(S)-3(R)- alcohol products as a residue. The ratio of 2(S)-3(S)-alcohol to 2(S)-3(R)-alcohol is about 85:15.

Step E:

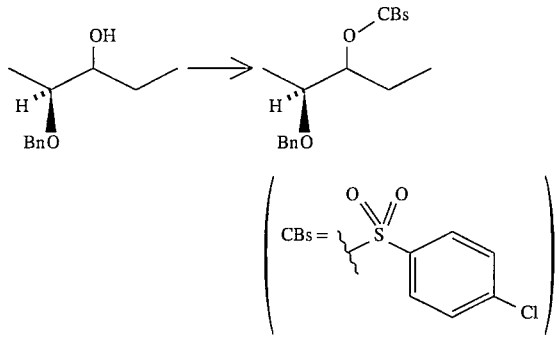

Combine 6.3 kg of the mixture of diastereomeric alcohols obtained as the product of Step D and 18.9 L of $CH_2Cl_2$ and stir while cooling to 0° to 5° C. Add 7.6 kg of p-chlorobenzenesulphonyl chloride. Slowly add a solution of 5.2 kg of DMAP in 18.9 L of $CH_2Cl_2$ while keeping the reaction temperature at <10° C. Stir the mixture at 15° to 25° C. until the reaction is complete by HPLC (about 16 hours). [HPLC analysis procedure: Extract a 1 mL aliquot of the mixture with dilute HCl (aqueous), then dilute to a volume of 250 mL with MeOH and analyze a 5 µL sample of that solution using a Zorbax® RxC8 column, and MeOH/water (75:25) as the mobile phase.] Add 6.3 L of 25% NaOH (aqueous) and 6.3 L of water to the mixture and stir at 15° to 25° C. for about 1 hour. Slowly add the resulting mixture to a mixture of 25.2 L of water, 31.5 kg of ice, and 2.5 L of $H_2SO_4$. Separate the layers and wash the organic layer successively with 63 L of 5% $NaHCO_3$ (aqueous), and water (2× 12.6 L). Concentrate the organic layer first by distillation at 60° C., then in vacuo at <60° C. to give a mixture of the chlorobenzenesulfonates of the 2(S)-3(S)- and 2(S)-3(R)- alcohols as a residue.

Step F:

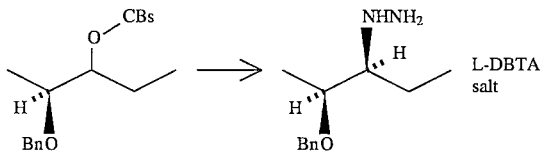

Combine 11.0 kg of the mixture of chlorobenzenesulfonates obtained as the product of Step E and 16.5 L of anhydrous EtOH, then add 11.0 L of hydrazine monohydrate and stir the mixture at 65° C. until the reaction is complete (about 16 hours). Cool to 15° to 25° C., add 11.0 L of water and 55.0 L of TBME, then stir for 15 min. Allow the mixture to settle, separate the layers and extract the aqueous layer with 55 L of TBME. Combine the organic layers and wash with water (2×11.0 L). Slowly add the organic solution to a solution of 11.0 kg of 1-DBTA in 110.0 L of TBME and stir at 15° to 25° C. for 2 hours. Filter to collect the resulting precipitate and wash the solid with 22.0 L of TBME. Dry the solid in a vacuum oven at 25° C.±5° C. to give the 2(S)-3(S)-chiral hydrazine product as its L—DBTA salt. (The ratio of 2(S)-3(S)-hydrazine to 2(S)-3(R)-hydrazine in the product is 91:9).

Step G:

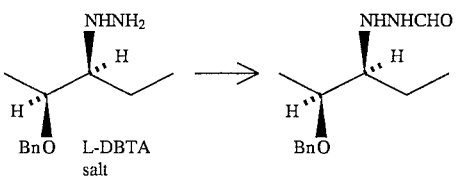

Combine 10 kg of the product of Step F, (alternatively, the product of Example 2 can be used), and 100 L of ethyl formate and heat the mixture at reflux for 1 to 2 hours until all of the solid is dissolved and the reaction is complete by HPLC. [HPLC analysis procedure: Combine 2 drops of the reaction mixture and 3 mL of 1% $Et_3N$ in MeOH and analyze using a Zorbax® Rx-C8 column, and MeOH/water (75:25) as the mobile phase.] Add 60.0 L of TBME, then add the resulting mixture to a mixture of 2.8 kg of $Na_2CO_3$ and 50 L of water and stir the mixture for 15 min. Allow the layers to settle, separate the layers, then wash the organic layer successively with a solution of 0.5 kg $NaHCO_3$ in 10 L of water, and a solution of 0.5 kg of NaCl in 10 L of water. Concentrate the organic solution in vacuo at a temperature of <40° C., add 60.0 L of $CH_2Cl_2$ and distill at atmospheric pressure at about 44° C. to give the title compound as a residue.

EXAMPLE 2

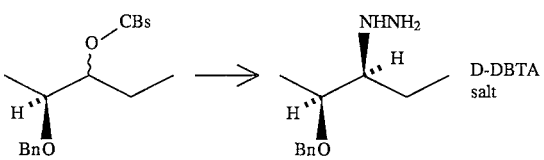

The mixture of 2(S)-3(S)- and 2(S)-3(R)-chlorobenzenesulfonates from Step E of Example 1 is converted to a mixture of the 2(S)-3(R)- and 2(S)-3(S)-hydrazines which are isolated as their D—DBTA salts using D—DBTA and substantially the same procedure as described in Step F of Example 1. The ratio of SS:SR isomers is 96:4, as compared to the 91:9 ratio obtained using L—DBTA as described in Example 1. Recrystallization of the D—DBTA salt from a suitable solvent, such as a mixture of TBME and EtOH, provides the 2(S)-3(S)-hydrazine having a ratio of SS:SR of >99:1. This D—DBTA hydrazine can be used in Step G of Example 1.

We claim:

1. A process for preparing a compound having the formula

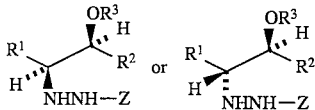

wherein:

$R^1$ and $R^2$ are independently $C_1$–$C_{10}$ alkyl;

$R^3$ is H or $R^4$ wherein $R^4$ is a hydroxy protecting group; and

Z is H, —CHO, —C(O)OC(CH$_3$)$_3$ or —C(O)OCH$_2$C$_6$H$_5$, comprising the steps:

(a) reacting a chiral compound of the formula

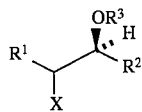

wherein

X is a leaving group, and $R^1$, $R^2$ and $R^3$ are as defined above, with hydrazine, to form a mixture of diastereomeric hydrazines of the formulae

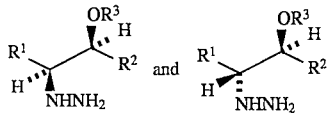

wherein $R^1$, $R^2$ and $R^3$ are as defined above, treating the mixture with a chiral acid to isolate the desired diastereomer as its chiral acid salt, and optionally regenerating the free hydrazine; and (b) treating the free hydrazine or the chiral acid salt of step (a) with a compound of the formula Y—Z, wherein Z is —CHO, —C(O)OC(CH$_3$)$_3$ or —C(O)OCH$_2$C$_6$H$_5$, and Y is a leaving group, to form the chiral hydrazine derivative.

2. The process of claim 1 wherein the chiral acid is selected from dibenzoyl-L-tartaric acid, dibenzoyl-D-tartaric acid, ditoluoyl-L-tartaric acid and ditoluoyl-L-tartaric acid.

3. The process of claim 2 wherein Z is —CHO and Y is $C_1$–$C_6$ alkoxy.

4. The process of claim 2 wherein Z is —C(O)OC(CH$_3$)$_3$, and Y is $C_1$–$C_6$ alkoxy.

5. A process for preparing a compound having the formula

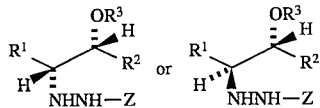

wherein:

$R^1$ and $R^2$ are independently $C_1$–$C_{10}$ alkyl;

$R^3$ is H or $R^4$ wherein $R^4$ is a hydroxy protecting group; and

Z is H, —CHO, —C(O)OC(CH$_3$)$_3$ or —C(O)OCH$_2$C$_6$H$_5$, comprising the steps:

(a) reacting a chiral compound of the formula

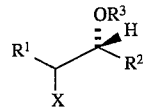

wherein

X is a leaving group and $R^1$, $R^2$ and $R^3$ are as defined above, with hydrazine, to form a mixture of diastereomeric hydrazines of the formulae

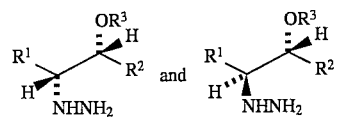

wherein $R^1$, $R^2$ and $R^3$ are as defined above, treating the mixture with a chiral acid to isolate the desired diastereomer as its chiral acid salt, and optionally regenerating the free hydrazine; and (b) treating the free hydrazine or the chiral acid salt of step (a) with a compound of the formula Y—Z, wherein Z is —CHO, —C(O)OC(CH$_3$)$_3$ or —C(O)OCH$_2$C$_6$H$_5$, and Y is a leaving group, to form the chiral hydrazine derivative.

6. The process of claim 5 wherein the chiral acid is selected from dibenzoyl-L-tartaric acid, dibenzoyl-D-tartaric acid, ditoluoyl-L-tartaric acid and ditoluoyl-D-tartaric acid.

7. The process of claim 6 wherein Z is —CHO and Y is $C_1$–$C_6$ alkoxy.

8. The process of claim 6 wherein Z is —C(O)OC(CH$_3$)$_3$, and Y is $C_1$–$C_6$ alkoxy.

* * * * *